United States Patent [19]
Roy

[11] Patent Number: 5,434,011
[45] Date of Patent: Jul. 18, 1995

[54] METHOD FOR MANUFACTURING A PEAT MOSS BOARD HAVING A PREDETERMINED DENSITY AND THE RESULTING PRODUCT THEREOF

[75] Inventor: Martin Roy, Quebec, Canada

[73] Assignee: Johnson & Johnson Inc., Quebec, Canada

[21] Appl. No.: 806,750

[22] Filed: Dec. 13, 1991

[51] Int. Cl.⁶ .......................... B32B 23/04; D01B 1/50
[52] U.S. Cl. ............................ 428/532; 428/105; 428/106; 428/156; 428/172; 428/182; 428/533; 428/534; 428/536; 156/219; 156/242; 264/175; 162/13; 162/92; 162/109; 162/150; 162/205

[58] Field of Search ................ 162/92, 148, 197, 205, 162/206, 13, 150, 109, 142, 227; 604/374, 375, 389, 904; 428/182, 105, 225, 229, 284, 913, 226, 106, 156, 172, 68, 131, 340, 402, 532, 533, 534, 535, 536; 156/62.2, 219, 209, 242; 264/115, 116, 121, 175, 517, 518

[56] References Cited

U.S. PATENT DOCUMENTS 4,473,440 9/1984 Ovans .................................. 162/205
4,992,324 2/1991 Dubé .................................. 428/226

Primary Examiner—Donald J. Loney

[57] ABSTRACT

A method for manufacturing a peat moss board suitable for use as an absorbent core in structures for absorbing body exudate. The method is characterized by conditioning a wet laid board to a specific water content and calendering the conditioned board at a predetermined pressure. The water content and the calendering pressure determine the density of the peat moss board in final form. The invention also extends to a peat moss board manufactured by the novel method.

16 Claims, 1 Drawing Sheet

METHOD FOR MANUFACTURING A PEAT MOSS BOARD HAVING A PREDETERMINED DENSITY AND THE RESULTING PRODUCT THEREOF

FIELD OF THE INVENTION

The present invention relates to a method for manufacturing a calendered, fluid absorbent board containing peat moss material, suitable for use as an absorbent core in disposable absorbent products such as sanitary napkins, tampons, diapers, adult briefs, urinary pads and the like. More particularly, the invention provides a method for controlling the density of the peat moss board by regulating the calendering pressure and the water content of the peat moss material during the calendering operation. The invention also extends to a calendered peat moss board manufactured by the novel method.

BACKGROUND OF THE INVENTION

The prior art has recognized the potential of peat moss material for use as an absorbent medium in structures for absorbing body exudate. Peat moss material has highly desirable fluid absorption properties such as a remarkable absorption capacity and the ability of "drying" adjacent materials by continuing to pull or wick fluid away from them over a long time period such that virtually all the fluid is collected in the peat moss core. These attributes allow the material to provide highly efficient absorbent components which can be made relatively thin for better fit, comfort and discretion, while being sufficiently absorbent to prevent overflow leakage and garment staining.

The following United States Patents document the use of peat moss material for manufacturing absorbent components for disposable absorbent products:

| U.S. Pat. No. | INVENTOR | DATE ISSUED |
|---|---|---|
| 4,170,515 | Lalancette et al. | October 9, 1979 |
| 4,215,692 | Levesque | August 5, 1980 |
| 4,226,237 | Levesque | October 7, 1980 |
| 4,305,393 | Nguyen | December 15, 1981 |
| 4,473,440 | Ovans | September 25, 1984 |
| 4,507,122 | Levesque | March 26, 1985 |
| 4,618,496 | Brasseur | October 21, 1986 |
| 4,676,871 | Cadieux et al. | June 30, 1987 |
| 4,992,324 | Dubé | February 12, 1991 |
| 5,053,029 | Yang | October 1, 1991 |

The subject matter of these references is incorporated herein by reference.

Peat moss material can be formed in a highly cohesive board by using any one of the methods disclosed in the above-identified prior art. In a board form, the peat moss material is convenient to handle and it can be directly processed in high speed automatic equipment for assembling disposable absorbent products.

More particularly, the method for producing the peat moss board consists of screening raw peat moss material in particulate form to retain only the particles which are the most absorbent. The screened fraction is then formed into a slurry which is sheeted on a Fourdrinier wire and dewatered by the application of vacuum. The thus formed board is dried and calendered to increase its density to the desired level. In order to tenderize, soften and improve the flexibility of the calendered peat moss board, it may be subjected to mechanical working such as perf-embossing and micro-corrugating as described in the U.S. Pat. Nos. 4,559,050 and 4,596,567 issued to Iskra on Dec. 17, 1985 and Jun. 24, 1986. The disclosure of these patents is incorporated herein by reference.

The prior art has recognized the importance of controlling certain variables during the manufacturing process of the board in order to maintain the absorbency of the final product within acceptable limits. In this regard, the U.S. Pat. No. 4,473,440 Ovans, issued on Sep. 25, 1984 is of interest. This reference teaches to regulate the water content of the absorbent board immediately before the calendering operation with relation to the weight percent of the peat moss material in the board.

It is also known to those skilled in the art that the density of the peat moss board is an important parameter which markedly influences its absorption properties and its comfort potential. In currently practised methods for manufacturing peat moss boards, the density control is achieved by trial and error which essentially consists of changing certain variables that are known to influence the density of the board, until the desired density of the final product is achieved.

Presently, the limited knowledge and understanding of the various factors determining the density of the peat moss board do not allow a strict and rigorous process control. As a result, undesirable fluctuations in the properties of the final product are difficult to avoid.

OBJECTS OF THE INVENTION

An object of the present invention is a method for manufacturing a board of peat moss material providing a control leverage over the density of the peat moss board.

Another object of the invention is a peat moss board manufactured by the novel method according to the present invention.

Additional objects of the invention will become apparent from the ensuing description.

SUMMARY OF THE INVENTION

As embodied and broadly described herein, the invention provides a method for manufacturing a peat moss board for use as a fluid absorbent component of a disposable absorbent structure, the peat moss board having a desired density D (for the purpose of this specification, all density values are measured at 12% moisture based on the weight of bone dry board) whose value is expressed in grams per cubic centimeter (g/cc), the method comprising the steps of:

forming a board comprising at least 45% by weight of peat moss material based on the weight of bone dry board;

conditioning the board to have a water content W expressed in weight percent based on the weight of bone dry board;

calendering the conditioned board at a pressure P expressed in pounds per linear inch (pli), wherein the values W and P are selected to satisfy the following relation:

$$(0.4409 \pm 0.0611) - D = 0.02122\ W - 0.000032\ P$$

This empirical relation may be conveniently used to set the calendering pressure P and the water content W of the peat moss board with relation to the value of D. By selecting the calendering pressure P and the water content W such that the right hand term of the equation is within the range determined by the extreme values provided by the left hand term, the actual density of the calendered board will vary by a maximum of 0.0611 g/cc from the desired density D.

To reach a precise density value within the density range determined by W and P, the actual density of the peat moss board is measured and any deviation is corrected by changing the values of the variables P and W. Objectively, this technique still involves trial and error adjustments, however the required manipulations are relatively small and they are needed only for fine tuning the board density.

The presence of two variables in the empirical relation provides two degrees of freedom to control the density of the peat moss board. This characteristic allows to set the value of one variable and control the density with the remaining one. For example, the water content W of the board may be set in accordance with the teaching of the above mentioned U.S. Pat. No. 4,473,440 to enhance the absorbency of the peat moss board. The calendering pressure P is then adjusted to provide the desired board density. The relative independence between the variables is highly advantageous because it allows more flexibility in terms of overall process control.

The value of P is dependent on the characteristics of the calendering equipment that is being used. In other words, different calendering stations may develop exactly the same pressure at the nip, thus conditioning the calendered material in the same way, albeit the pressure reading in pli is different for each station.

For the purpose of this specification, a given value of P will express an actual nip pressure which is equivalent to the pressure represented by the value of P and developed at the nip of a calendering station having the following characteristics:

1) a top roll having a diameter of 16.901 inches, a length of 36 inches, a hardness of 75/82 shore C and a crown of 0,00455 inches;
2) a bottom roll having a diameter of 17.978 inches, a hardness of 76/80 shore C, a length of 36 inches and a crown of 0.00415; and
3) speed of 1.8 meters per minute.

As embodied and broadly described herein, the invention also provides a calendered peat moss board manufactured by the process of the invention.

BRIEF DESCRIPTION OF THE DRAWING

The annexed drawing graphically illustrates the relationship between the density of the peat moss board, the calendering pressure and the water content of the board.

DESCRIPTION OF A PREFERRED EMBODIMENT

Figure 1:
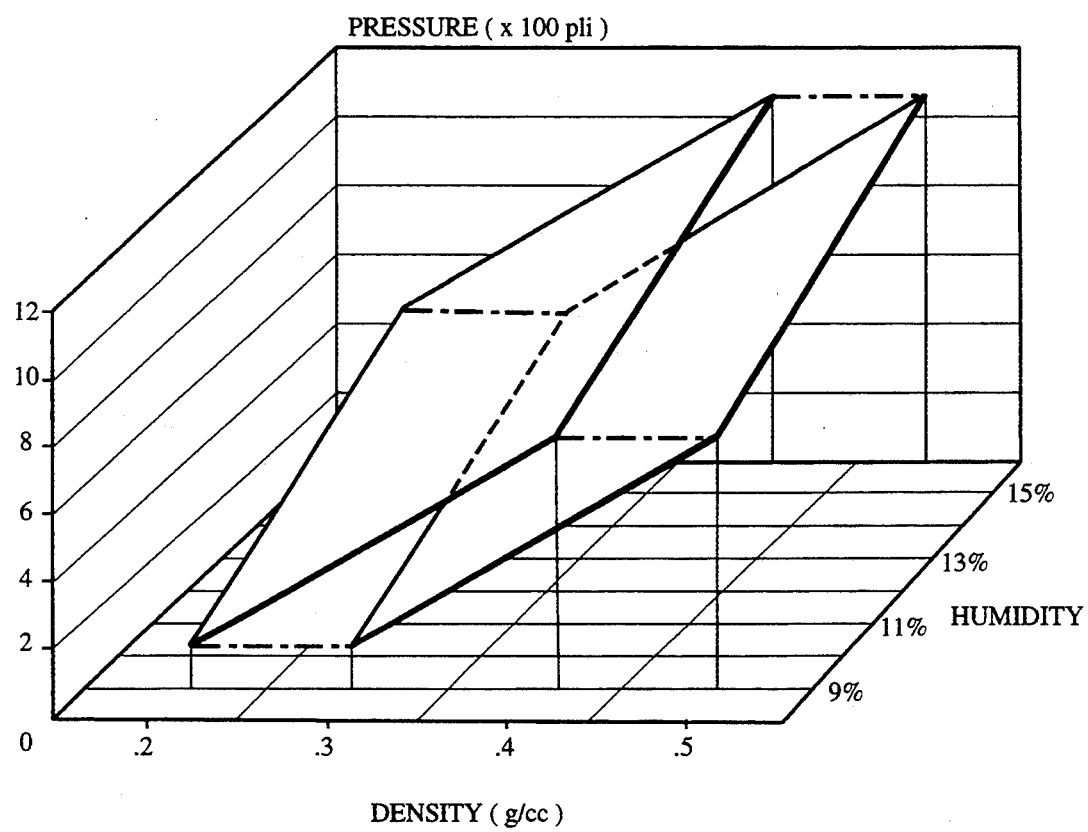

The starting peat moss harvested from the bog should have a relatively high absorbent capacity. Peat moss capable of absorbing and retaining at least about 25 and preferably about 50 times its weight in water has been found satisfactory.

The starting peat moss is wet classified to remove the extremely fine material, commonly referred to as fines, and large pieces of material including roots, branches and the like which do not contribute significantly to the absorbency of the peat moss material.

The classification is carried out such that anything that remains on a number 10 mesh screen (2000 microns) is discarded and anything that passes through a number 200 mesh screen (74 microns) is also discarded. Preferably, anything that remains on a number 14 mesh screen (1410 microns) is discarded and anything that passes through a number 100 mesh screen (149 microns) is discarded.

The classification is carried out by a wet screening process which consists of forming an aqueous slurry of the peat moss material and flowing the slurry through successive screening stages to extract from the slurry the fines and the excessively large particles.

The screened peat moss fraction is diluted with water to a manageable slurry. If desired, a fibrous component may be added to the slurry. The fibrous component may include such materials as KRAFT® wood pulp and mechanical wood pulp. As used herein, the term mechanical wood pulp is meant to include ground wood pulp, thermo-mechanical pulp and refiner wood pulp. Ground wood is essentially trees and branches which have been debarked, cleaned and then ground into particulate matter. Refiner wood pulp differs from ground wood pulp only in that the grinding step utilizes a refiner, i.e. a disc-like device well known in the art and generally having metallic ribs at the peripheral sections thereof which last contact the wood particles and help separate the wood fibers without excessively damaging them. Thermo-mechanical wood pulp is similar to refiner pulp with the exception that the wood particles are heated when in the refiner, usually with steam, and this heating further aids in separating the wood fibers. The common characteristic of these mechanical pulps is that no attempt has been made to separate the fibers by chemical means although they may later, after being reduced to fine particulate matter, be subjected to a desired chemical treatment.

Preferably, when the mechanical wood pulp is used in the board of this invention such mechanical wood pulp has a Canadian Standard Freeness (TAPPI test method T-227) of from about 60 to 750 and preferably from about 400 to 600.

The KRAFT® wood pulp, also usable in combination with the peat moss, is essentially chemically treated, long fibered pulp such as sulfite and sulfate wood pulps.

The fibrous component may also include a natural or synthetic textile fiber such as rayon, polyester, nylon, acrylic or the like, having a length of from about 0.25 to 0.75 inches, preferably about 0.5 inches and a denier of from about 1.0 to 5 and present in an amount from about 2 to 20% by weight, most preferably from 4 to 8%.

The slurry is sheeted onto a Fourdrinier wire and dewatered to form a starting board. The slurry may range from about 0.1 to about 1% solids and other ingredients may be added to the slurry such as, for example, coloring agents, wetting agents, adhesives, or the like. After passing the slurry onto the Fourdrinier wire, initial dewatering may take place under the influence of vacuum to render the water content to about 5 parts by weight of water per part by weight of solids.

The density of the board may be controlled by varying such factors as the pressure difference during the vacuum dewatering and the speed of the Fourdrinier wire. Generally, decreased vacuum and increased speed will result in a less dense product. A suitable low density peat moss board can be produced with a board lay down of from 15 to 35 grams of solid per square foot of board and for a vacuum pressure of from 10 to 15 inches of mercury. The speed of the Fourdrinier wire and the width of the vacuum slot under which the board is exposed to the pressure differential of the vacuum should be varied so as to create a residence time of the board over the vacuum slots of about 1 to about 5 seconds. For example, with 2 slots each having a 1 inch width, a Fourdrinier wire speed of about 2.5 feet per minute results in a residence time of about 1.5 seconds which, with a lay down of 20 grams per square foot, produces a low density board. Similarly, with 4 slots, each with a 1 inch width, a Fourdrinier speed of 1.7 feet per minute results in a residence time of 4.4 seconds and also produces a low density peat moss board. In each of the above examples, a vacuum of about 12 inches of mercury is maintained.

Irrespective of the choice of parameters chosen, the resulting board, prior to calendering is of low density, generally from about 0.04 to about 0.12 gm/cc.

In a specific embodiment of this invention, a laminate is made from the board and a layer of KRAFT® wood pulp. Preferably, the KRAFT® wood pulp is first laid down on a Fourdrinier wire from a slurry which can be about 0.1% solids. The KRAFT® slurry is dewatered and then passes to a second station where the peat moss and additives is laid directly on top of the KRAFT® layer. This composite layer may be dewatered to produce a laminate of the low density peat moss board described herein having a layer of KRAFT® pulp adhered to its surface. It is preferred that the KRAFT® employed be bleached and have a Canadian Standard Freeness of relatively high value, e.g. about 450 to 750. While the proportions of the KRAFT® layer to the peat moss board are not critical, a suitable product results when the layer of about 0.5 to 5 grams of KRAFT® wood pulp per square foot is employed. In addition, the strength characteristics of the laminate are greater than that which would result when the peat moss board is used alone.

If desired, a KRAFT® wood pulp layer may also be laid on top of the peat moss layer to form a sandwich-like structure comprising a central peat moss core covered by two layers of KRAFT® wood pulp. This form of construction further enhances the strength characteristics of the board.

In accordance with the teachings of the invention, the dewatered, low density peat moss board is conditioned to a specific water content level and then calendered at a predetermined pressure, selected in accordance with the desired density of the final product. The moisture content conditioning can be accomplished by drying the low density board down to the prescribed moisture level and then calendering. The resulting product may then be further dried in a second stage drier, or simply be allowed to equilibrate to its normal ambient water content. Alternatively, the dewatered board may be dried to ambient water content in a first stage drier and then water may be added, in a conditioning chamber, to increase the moisture content to a higher desired level.

Both methods have advantages and the choice will be determined by the manufacturers weighing of these advantages. For example, by drying the dewatered board to the prescribed level and then calendering, there is an energy savings realized in the drying process in that only the required amount of water is actually removed from the peat moss board. On the other hand, by drying to a low level and then adding water in a conditioning chamber, the process is more controllable and closer moisture content tolerances may be maintained.

The conditioned board is calendered by passing the board between the nip defined by calender rollers.

The invention provides a relationship allowing to express the calendering pressure P and the water content W in terms of the desired density D of the board at 12% moisture based on the weight of bone dry board of the peat moss material. The relation is as follows:

$$(0.4409 \pm 0.0611) - D = 0.02122W - 0.000032P$$

Preferably, P varies between 3000 to 9000 pli.

This relation applies to boards having a peat moss concentration of from about 45% to about 100%, the balance being preferably formed by any of the additives mentioned earlier.

In accordance with this equation, the water content W and the calendering pressure P are selected whereby the value of the right hand term of the equation is within the range determined by the extreme values of the left hand term. The density of the calendered board is then measured and any deviation from the desired density value D is compensated by adjusting slightly W or P, or both. The density of the calendered board is measured again and any residual error is compensated in the same way. This step is repeated until the predetermined density value D is reached.

The following example illustrates the advantages derived from the present invention.

Raw peat moss material is classified into a fraction having a particle size from about 250 microns to about 1880 microns. The classified fraction is combined with polyester and KRAFT® wood pulp fibers in the following proportions:

| INGREDIENTS | PARTS BY WEIGHT* |
| --- | --- |
| Peat moss | 76.8% |
| Polyester fibers | 4.9% |
| KRAFT® wood pulp fibers | 7.9% |

*Based on the weight of the bone dry calendered board.

This solid mixture is dispersed in water to form an aqueous slurry having a consistency of 1.3% by weight solids. The slurry is sheeted on a Fourdrinier wire over a layer of KRAFT® wood pulp fibers previously deposited on the wire. Downstream of the point at which the slurry is deposited, a layer of KRAFT® wood pulp fibers is laid on the slurry to form a sandwich-like structure in which the peat moss slurry forms the central layer. The parts by weight of the KRAFT® wood pulp fibers based on the weight of de-moisturized calendered board is 9.8% equally distributed between the top and the bottom layers.

The thus formed board is treated with a wetting agent manufactured by the Clough Chemical Company and commercialized under the name THROWET G-60. The part by weight of wetting agent based on the weight of demoisturized calendered board is 0.65%.

The board is dewatered by the application of vacuum and then dried to reach a moisture level of 12%. Immediately after the board has been conditioned to the desired water content, it is calendered at 5000 pli.

According to these operating conditions, the relationship between the density, water content and calendering pressure indicates that actual density of the calendered board, at 12% moisture based on the weight of bone dry board will be situated in the range from 0.3 g/cc and 0.5 g/cc. The measured density of the calendered board is 0.38 g/cc, thus confirming the relation.

FIG. 1 illustrates the density of the calendered board as a function of the moisture content and the calendering pressure for peat moss concentrations in the range from about 45% to about 100%. The collection of points which satisfy the relationship is a volume defined by a pair of parallel planes.

Before incorporating the calendered board into a disposable absorbent product, it is preferably subjected to a mechanical tenderizing operation such as perf-embossing or micro-corrugating to improve the flexibility of the board. The perf-embossing and micro-corrugating processes are described in detail in the U.S. Pat. Nos. 4,596,567 and 4,559,050 mentioned earlier.

The scope of the present invention is not limited by the description, examples and suggestive uses herein, as modifications can be made without departing from the spirit of the invention. Application of the product and the methods of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

I claim:

1. A method for manufacturing a peat moss board for use as a fluid absorbent component of a disposable absorbent structure, said peat moss board having a desired density D expressed in grams per cubic centimeter (g/cc), said method comprising the steps of:
   forming a board comprising at least 45% by weight of peat moss material based on the weight of bone dry board;
   conditioning said board by adding or removing moisture such that it will have a water content W expressed in weight percent based on the weight of bone dry board;
   calendering the conditioned board at a pressure P expressed in pounds per linear inch (pli), wherein the values W and P are selected to satisfy the following relation:

$$(0.4409 \pm 0.0611) - D = 0.02122\ W - 0.000032\ P$$

2. A method as defined in claim 1, wherein the step of forming said board of peat moss material includes the steps of:
   forming a slurry of peat moss material;
   sheeting said slurry; and
   dewatering the sheeted slurry.

3. A method as defined in claim 2, further comprising the step of classifying the peat moss material to eliminate therefrom particles having a size substantially smaller than 74 microns and particles having a size substantially larger than 2000 microns.

4. A method as defined in claim 3, comprising the step of combining with said peat moss material a component selected from the group consisting of polyester, nylon, acrylic, wood pulp, synthetic wood pulp, thermomechanical pulp, mechanically ground pulp, wetting agent and mixtures thereof.

5. A calendered peat moss board manufactured by the method of claim 3.

6. A calendered peat moss board as defined in claim 5, wherein said board has a laminated structure.

7. A calendered peat moss board as defined in claim 6, comprising a first layer of peat moss material and a layer of KRAFT® wood pulp.

8. A calendered peat moss board as defined in claim 6, comprising a central layer made of peat moss material between layers of KRAFT® wood pulp.

9. A calendered peat moss board as defined in claim 5, wherein said board is perf-embossed.

10. A calendered peat moss board as defined in claim 5, wherein said board is micro-corrugated.

11. A method as defined in claim 2, comprising the step of sheeting said slurry on a layer of pulp fibers, whereby dewatering of said slurry causes said pulp fibers to adhere to said peat moss material.

12. A method as defined in claim 2, comprising the step of depositing over the sheeted slurry a layer of pulp fibers, whereby dewatering of said slurry causes said pulp fibers to adhere to said peat moss material.

13. A method as defined in claim 11 or claim 12 wherein said pulp fibers are KRAFT® wood pulp fibers.

14. A method as defined in claim 1, further comprising the steps of:
   a) measuring the density of the calendered peat moss board;
   b) comparing the value of density obtained at step (a) with D to determine a difference therebetween;
   c) varying one of W and P in order to reduce said difference.

15. A method as defined in claim 14, further comprising the step of repeating steps a, b and c until said difference is nullified.

16. A method as defined in claim 1, further comprising the step of subjecting said calendered peat moss board to a treatment selected from the group consisting of perf-embossing and micro-corrugating.

* * * * *